(12) United States Patent
Flor et al.

(10) Patent No.: US 7,862,779 B2
(45) Date of Patent: Jan. 4, 2011

(54) VISUAL SPILL INDICATING

(75) Inventors: Nicolo Flor, Oakville (CA); John Christopher Polis, St. Catharines (CA); Richard H. Hall, Midland, MI (US)

(73) Assignee: Imbibitive Technologies Corporation, Wilmington, DE (US)

( * ) Notice: Subject to any disclaimer, the term of this patent is extended or adjusted under 35 U.S.C. 154(b) by 1142 days.

(21) Appl. No.: 11/507,925

(22) Filed: Aug. 22, 2006

(65) Prior Publication Data

US 2007/0048876 A1    Mar. 1, 2007

Related U.S. Application Data

(60) Provisional application No. 60/711,186, filed on Aug. 25, 2005.

(51) Int. Cl.
*G01N 21/75* (2006.01)
*G01N 1/00* (2006.01)

(52) U.S. Cl. .................... 422/119; 436/166
(58) Field of Classification Search ............. 422/119; 436/166
See application file for complete search history.

(56) References Cited

U.S. PATENT DOCUMENTS

| | | | |
|---|---|---|---|
| 3,750,688 A | 8/1973 | Hall et al. ............. | 137/2 |
| 4,232,552 A * | 11/1980 | Hof et al. ............. | 374/106 |
| 4,302,337 A | 11/1981 | Larson et al. ......... | 210/662 |
| 4,313,393 A | 2/1982 | Barbuscio et al. ..... | 116/200 |
| 4,615,828 A * | 10/1986 | Wegrzyn .............. | 252/408.1 |
| 4,822,743 A | 4/1989 | Wegrzyn .............. | 436/3 |
| 5,154,887 A | 10/1992 | Babb et al. .......... | 422/56 |
| 5,270,209 A | 12/1993 | Rigg et al. ........... | 436/39 |
| 5,550,061 A | 8/1996 | Stone ................. | 436/73 |
| 5,788,942 A | 8/1998 | Kitani et al. ......... | 422/56 |
| D400,973 S | 11/1998 | Hall et al. ........... | D23/365 |
| D400,974 S | 11/1998 | Hall et al. ........... | D23/365 |
| D403,059 S | 12/1998 | Flor et al. ........... | D23/365 |
| D403,060 S | 12/1998 | Flor et al. ........... | D23/365 |
| D403,418 S | 12/1998 | Brinkman et al. ...... | D23/365 |
| D415,831 S | 10/1999 | Hall et al. ........... | D23/365 |
| D419,652 S | 1/2000 | Hall et al. ........... | D23/259 |

(Continued)

FOREIGN PATENT DOCUMENTS

EP    0608884    8/1994

(Continued)

OTHER PUBLICATIONS

Hall et al., U.S. Appl. No. 10/311,815, filed on Dec. 19, 2002 A.D.

(Continued)

*Primary Examiner*—Lore Jarrett
(74) *Attorney, Agent, or Firm*—Christopher John Rudy

(57) ABSTRACT

Composition has an indicating dye encapsulated by an encapsulating material. An encapsulated indicating dye can be combined with an organic substance absorbent and/or adsorbent. The composition, combination and/or a device having one or both of them can be used to indicate the presence of an organic substance by contacting the same with a sample, and, ascertaining whether an appropriate color release occurs to indicate the presence of the organic substance by contact of the organic substance with the composition, combination and/or device.

18 Claims, 3 Drawing Sheets

U.S. PATENT DOCUMENTS

| | | | |
|---|---|---|---|
| D428,108 S | 7/2000 | Flor et al. | D23/209 |
| 6,162,646 A | 12/2000 | Webster et al. | 436/166 |
| D441,067 S | 4/2001 | Flor et al. | D23/365 |
| 6,376,252 B1 | 4/2002 | Van Lente et al. | 436/66 |
| 6,576,473 B1 | 6/2003 | Scaringe et al. | 436/169 |
| 6,582,657 B2 | 6/2003 | Warner et al. | 422/56 |
| 6,767,090 B2 | 7/2004 | Yatake et al. | 347/100 |
| 6,905,653 B1 | 6/2005 | Higuchi | 422/56 |
| 7,704,750 B2 | 4/2010 | Hall et al. | |
| 2004/0146641 A1* | 7/2004 | Hobbs et al. | 427/212 |
| 2005/0196343 A1 | 9/2005 | Reddy et al. | |

FOREIGN PATENT DOCUMENTS

| | | |
|---|---|---|
| EP | 1291397 | 3/2003 |
| WO | WO01/98757 | 12/2001 |

OTHER PUBLICATIONS

Search Report, Eur. pat. appl. No. 06394017.5-2204, report issued Dec. 7, 2006 A.D., with annex.

Aftenposten, "Reindeer hair eyed for mopping up oil spills," by Rapp, O.M., www.aftenposten.no, Jan. 30, 2007 A.D., downloaded Feb. 3, 2007.

Flor et al., U.S. Appl. No. 60/711,186, filed Aug. 25, 2005 A.D.

Article 96(2)EPC communication of Sep. 25, 2007 in European patent application No. 06394017.5-2204.

Data sheet for EP1291397 Ink Set for Ink-Jet Recording (esp@cenet document view) Dec. 12, 2007.

European patent application publication No. EP 1 757 931 A1, Feb. 28, 2007.

* cited by examiner

VISUAL SPILL INDICATING

This claims priority benefits of U.S. provisional patent application No. 60/711,186 filed on Aug. 25, 2005 A.D. In the United States of America, such is claimed under 35 USC 119(e), and, with respect to matters concerning the United States Patent and Trademark Office, the specification of the '186 provisional application is incorporated herein by reference.

FIELD AND PURVIEW OF THE INVENTION

The present invention concerns an indicator for the presence of organic substances, which, for example, may be found in spills and so forth. Generally, the indicator is encapsulated, and, desirably, it is accompanied by an organic substance absorbent, adsorbent or combination of the two, hereinafter, "absorbent and/or adsorbent," which, preferably, is a polymeric absorbent or imbiber for the organic substance that may be contained in a suitable device. Accordingly, in general, such an indicator composition, a combination and/or device with the composition and the absorbent and/or adsorbent, and methods of making and using the composition, combination and/or device can be of concern.

BACKGROUND TO THE INVENTION

Hall et al., WO 01/98757, discloses a visual spill indicator, which, in nature and gist, includes a composition that has a dye that changes color when contacted with a suitable amount of an organic substance, in conjunction with a matrix, paste, support, or web, to indicate visually or photometrically the presence of the organic substance. A beneficial embodiment employs the dye with a water-dissolving paper such that upon contact with water the paper dissolves to allow dye enfolded in the paper to contact an organic contaminant in a spill to indicate its presence.

As desirable and useful as that is, it would be desirable to improve upon the same. In particular, it would be desirable to provide for increased stabilization of the dye in such a system.

A FULL DISCLOSURE OF THE INVENTION

In general, this invention provides, in a foundational aspect, a composition comprising an indicating dye encapsulated by an encapsulating material. Provided also is an encapsulated indicating dye in combination with an organic substance absorbent and/or adsorbent, i.e., sorbent, which may further be contained in a suitable device. A method of making the composition can comprise providing an indicator dye, and encapsulating it by an encapsulating material; and of making the combination, by providing an encapsulated indicator dye, and bringing it into association with an organic substance absorbent and/or adsorbent, which may be brought into further association with a containing device for the same. The composition, combination and/or device can be used to indicate the presence of an organic substance by contacting the same with a sample, and, ascertaining whether an appropriate color release occurs to indicate the presence of the organic substance by contact of the organic substance with the composition, combination and/or device.

The invention is useful as an organic substance indicator.

Significantly, by the invention, the art is advanced in kind. An indicating dye is encapsulated, thus rendering it more stable in storage or waiting for activation in the field, especially, in a preferred embodiment, for employment with an organic substance absorbent, which is most beneficially used in an aqueous system that may contain an organic contaminant.

Numerous further advantages attend the invention.

The drawings form part of the specification hereof. With respect to the drawings, which are not necessarily drawn to scale, the following is briefly noted:

FIGS. 1-8 depict a sequence in which the invention, the encapsulated indicator dye particle composition of which is embodied in combination with a sorbent of Imbiber Beads Ⓡ from Imbibitive Technologies Corp., Wilmington, Del., U.S.A., St. Catharines, Ontario, Canada, to indicate the presence of and absorb an organic substance, say, diesel fuel and/or gasoline. As to FIG. 1, its reference time is zero minutes, and it shows an Imbiber Beads Ⓡ absorbent packet having the dye particle composition in the packet, and shows a basin with water; as to FIG. 2, its reference time is zero minutes, and it shows the packet of FIG. 1 in the basin with the water; as to FIG. 3, its reference time is zero minutes, and it shows diesel fuel being poured into a lab bottle; as to FIG. 4, its reference time is zero minutes, and it shows the diesel fuel being poured into the basin with the water; as to FIG. 5, its reference time is fifteen seconds, and it shows the packet starting to absorb the diesel fuel while activating the dye particle composition in the packet (turning red); as to FIG. 6, its reference time is one minute, and it shows the packet continuing to absorb the diesel fuel while the dye particle composition in the packet becomes progressively more activated (increasing redness); as to FIG. 7, its reference time is five minutes, and it shows the packet continuing to absorb the diesel fuel while the dye particle composition in the packet becomes progressively more activated (becomes redder); and as to FIG. 8, its reference time is fifteen minutes, and it shows the packet to have absorbed all diesel fuel while the dye particle composition in the packet becomes progressively more activated (continues to become more red).

Figure 1:
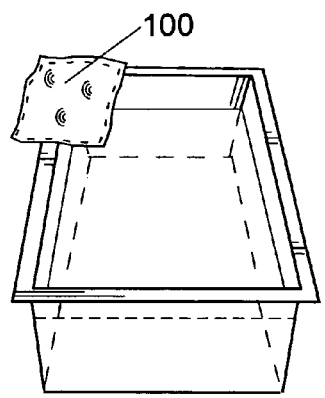
Figure 2:
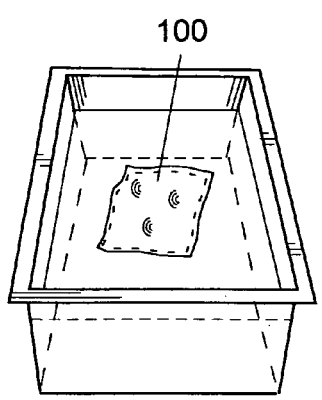
Figure 3:
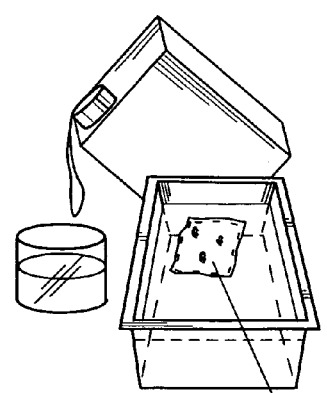
Figure 4:
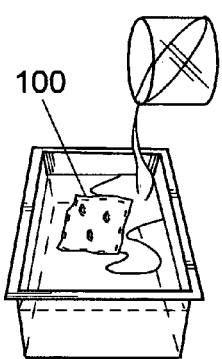
Figure 5:
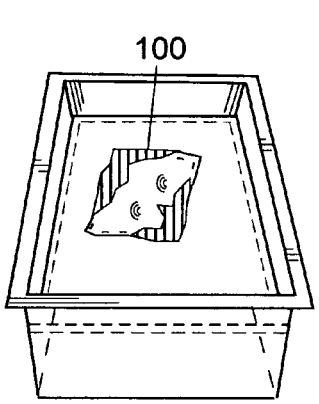
Figure 6:
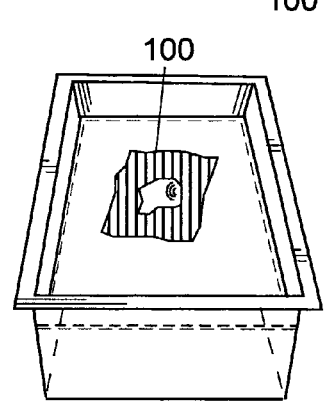
Figure 7:
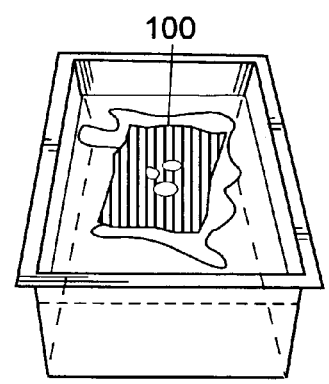
Figure 8:
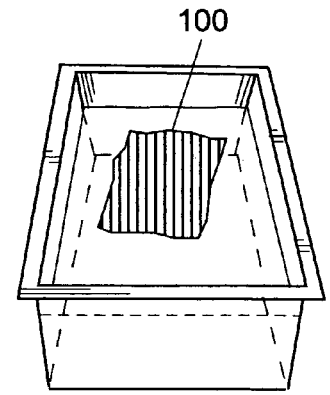
Figure 9:
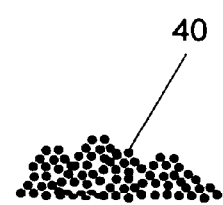
FIG. 9 depicts the composition itself employed in FIGS. 1-8, in a phase indicating the presence of the oleaginous substance.

FIG. 12 depicts the invention in various other embodiments. As to FIG. 12A, it shows a see-through pipe; as to FIG. 12B, it shows a pillow; as to FIG. 12C, it shows a boom and blanket floating on water; as to FIG. 12D it shows a pouch by which a bottle containing liquid is placed within the pouch, which is then placed in a vapor resistant film bag (not illustrated), with the bottle, pouch and bag then being placed within a can along with a cushioning material with a lid secured (not illustrated); as to FIG. 12E, it shows a see-through valve; and as to FIG. 12F, it shows a loose mix.

The invention can be further understood by the detail below, which may be read in view of the drawings. Such is to be taken in an illustrative and not necessarily limiting sense.

Any suitable indicator dye may be encapsulated. The dye can be a compound or mixture of compounds that indicate the presence of an organic substance by coloring the organic substance when contacted by a suitable amount of the organic substance. The organic substance is desirably in liquid form. The color change can include light in any suitable wavelength of any portion of the spectrum, to include X-ray, UV, visible, IR, and so forth parts; and so forth. Many suitable indicator dyes are highly colored solids, which appear in solid form to be very dark but when diluted and typically dissolved in the organic substance show a more recognizable color. For example, Oil Red A appears to be almost black as a solid until dissolved in an oil whereupon it appears red. The indicator dye may be advantageously selected from the class of anthracene, azo, anthraquinone, pyrazoline, or quinone, and so forth and the like type dyes. Beneficially, the indicator dye is hydrophobic and organo- or oleophilic, i.e., substantially if not essentially water insoluble but soluble in the organic substance, which may be a contaminant, of interest, for example, in gasoline or oil. A combination of indicator dyes may be employed with benefit herein. Accordingly, the indicator can be a typical dye such as Oil Red "A" (Solvent Red 24), i.e., 1-[[2-methyl-4-(2-methylphenyl)-azophenyl]azo]-2-naphthaleneol; another red dye such as a diazo or monoazo quin(n)aphthalone type compound; a yellow dye, for example, p-dimethylaminoazobenzene; another yellow dye such as a pyrazolone type compound; a blue dye, for example, Indanthrene Blue "R" (Dark Blue); another blue dye such as a monoazoanthroquinono type compound; a black dye such as an azo dye, many of which are proprietary compositions, for example, LX-6532 "Pylakrome Black," available from Pylam Products Co., Inc., Tempe, Ariz., U.S.A., and so forth. Preferably, the indicator dye employed is Retinol 50C or Solvent Red 26, especially the latter. A blue and/or yellow dye can also be desirable candidate(s). Indicator dye(s) that produce(s) an orange coloration with the organic substance can be beneficially employed in the practice of the invention.

Any suitable method for encapsulation may be employed, which method(s) those of skill in the encapsulation art recognize. Any suitable encapsulating material may be employed. For instance, an organic substance soluble material, in preference to or at least in conjunction with an aqueous soluble material, is beneficially employed. A suitable acrylate polymer or copolymer may be selected as the encapsulating material, which would desirably be soluble, as beneficially would be any other selected encapsulating material, in the target organic substance(s) that may be expected to be encountered in the field for sorption, for instance, class I chemicals or mixtures, which have high flash points, for example, gasoline, benzene, toluene, octane, heptane, hexane and pentane; and class II chemicals or mixtures, which have higher flash points, for example, kerosene, diesel fuel, jet fuels and mineral oil, heating oil, light machine oil, and so forth. Also, motor oil, transformer oil or crude oil, and/or distillation or reactor bottoms may be expected to be encountered in the field and can fall within the practice of the present invention. Thus, an oleaginous substance may be the target. Other materials may be present in the encapsulating material, for example, in addition to a primary polymeric component such as the acrylate polymer or copolymer. Preferably, the encapsulating material is an acrylate copolymer such as provided by Lipo Technologies, Inc., Vandalia, Ohio, U.S.A.

Any suitable amount of the indicator dye to the encapsulating material may be employed; for instance, ratios by weight of indicating dye to encapsulating material may be 10:1 to 1:10, preferably 9.5:1 to 3:1, which ratios may be considered to be approximate if not exact. A first combination can be ninety parts indicator dye and ten parts encapsulating material, a second seventy parts indicator dye and thirty parts encapsulating material, and a third fifty parts indicator dye and fifty parts encapsulating material, which parts are listed by weight and may be considered to be approximate if not considered exact, with the first combination, say, for a class II target such as diesel, the second, say, for a class I target such as gasoline, and the third, say, for a highly volatile organic target such as acetone. For an example, the first combination can be 90.9 percent by weight Solvent Red 26 encapsulated with 9.1 percent by weight of Lipo's acrylate copolymer. Any suitable size or shape for the encapsulated dye may be provided. Beneficially, the encapsulated dye composition is in a form of a particle fifty to two thousand microns in diameter, preferably one hundred to one thousand microns in diameter, and more preferably two hundred to five hundred microns in diameter, say, with target or obtained diameters of two hundred forty-two or two hundred seventy-eight microns, which sizes may be considered to be approximate if not considered to be exact.

Any suitable amount of the encapsulated indicator dye composition may be employed, to include when employed in conjunction with a sorbent. Beneficially, when employed in conjunction with the sorbent such as Imbiber Beads ® particles, which can imbibe up to an 850-mL quantity of a class I chemical or up to an 590-mL quantity of a class II chemical, ratios of encapsulated indicator dye composition to sorbent, which ratios may be considered to be approximate if not exact, can be 1:10 to 1;10000, preferably 1:50 to 1:1000, more preferably 1:100 to 1:200 to include 1:140 to 1:175, for example, 1:157 as may be found with a 0.7-g sample of the acrylic copolymer encapsulated Oil Red 26 as 90.9 percent by weight dye and 9.1 percent by weight encapsulating copolymer and a 110-g, 7-inch by 7-inch packet from Imbibitive Technologies Corp. having the noted Imbiber Beads ® particles.

Any suitable sorbent may be employed, to include those described in U.S. Pat. Nos. 3,750,688 and 4,302,337 and in the WO 01/98757 publication, or otherwise known in the art. Most preferably, however, the sorbent is an absorbent, especially an imbibing polymeric material as known in the art. See, e.g., the WO 01/98757 publication. The imbibing polymeric material can be a lightly cross-linked polyalkylstyrene copolymer such as found in the '688 patent, or commercially obtained, for example, from Imbibitive Technologies Corp. Such an imbibing polymeric material can be in the form of particles, which may be fifty to one thousand microns in diameter, preferably eighty to four hundred eighty microns in diameter, say, one hundred twenty five to four hundred twenty microns in diameter, with a target bead size of two hundred eighty-seven microns in diameter (fifty mesh), which sizes may be considered to be approximate if not considered to be exact. Preferably, the lightly cross-linked polystyrenic imbibing polymer or copolymer material is commercially available Imbiber Beads ® particles from Imbibitive Technologies Corp.

Figure 10:
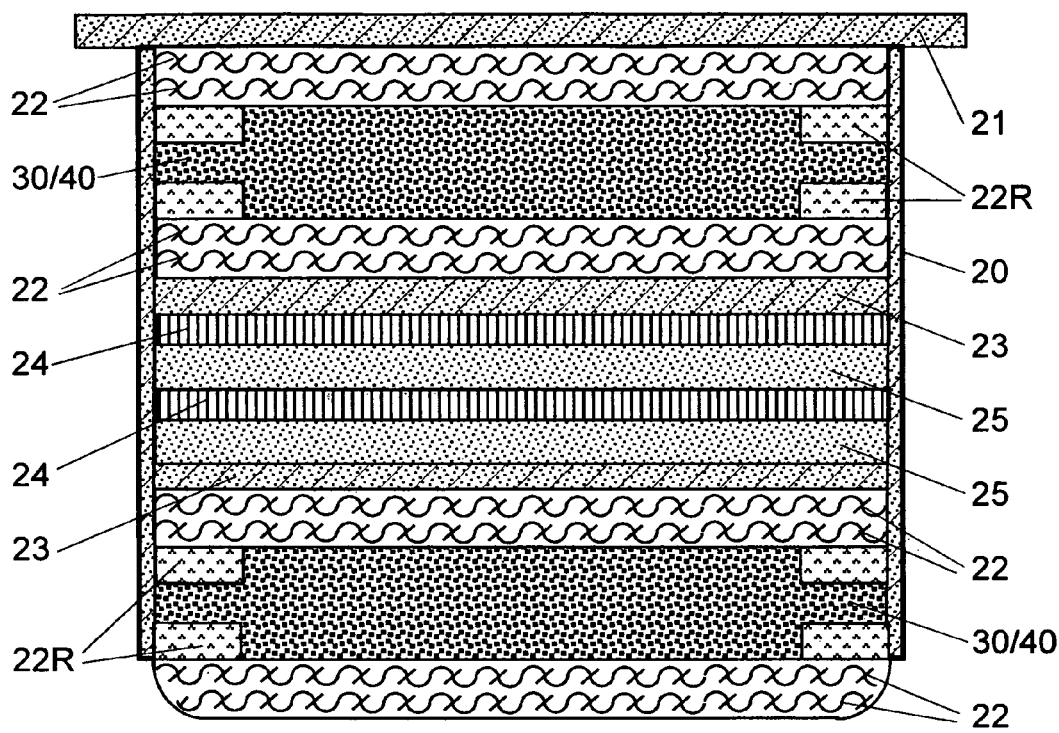
FIG. 10 depicts in cross section a device containing encapsulated indicator dye particles in combination with particles of a sorbent for organic substances.
Figure 11:
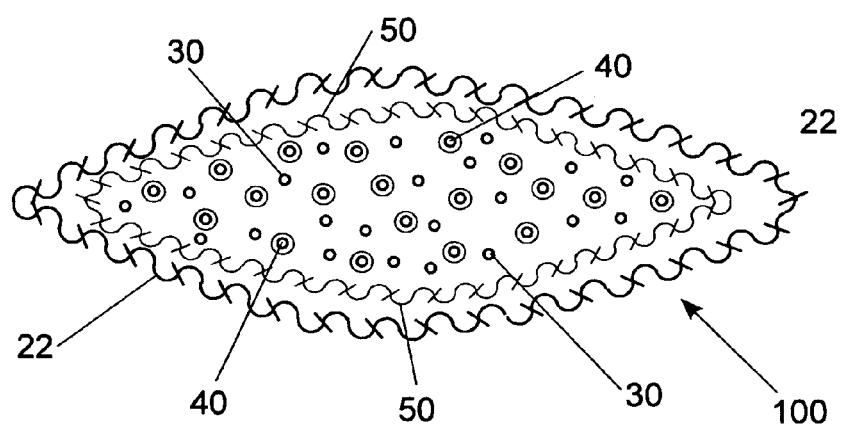
FIG. 11 depicts a cross-section of a packet of the invention further having a stand-off layer.
Figure 12A:
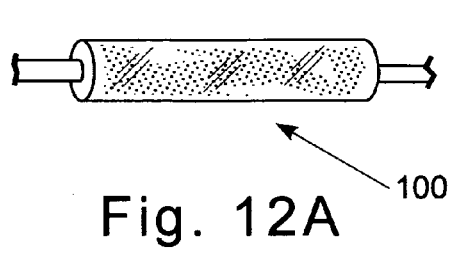
Figure 12B:
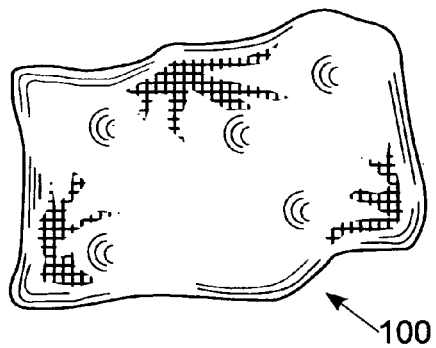
Figure 12C:
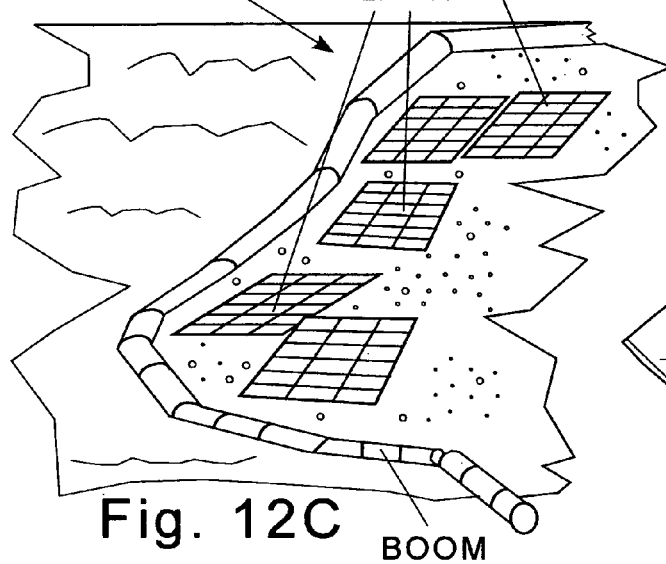
Figure 12D:
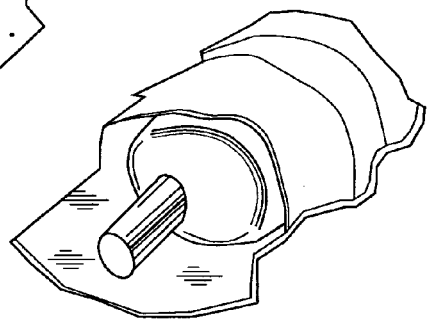
Figure 12E:
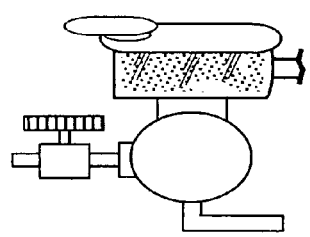
Figure 12F:
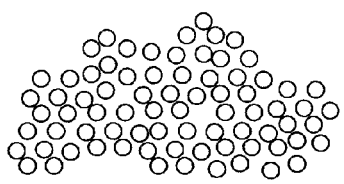

With reference to the drawings, device 100 includes containment housing 20, sorbent particles 30, and composition 40 of indicating dye encapsulated by an encapsulating material. The containment housing 20 can be of any suitable material or shape, and may be embodied in a packet (FIGS. 1-8), say, having its outer layer of spun-bond, nonwoven polypropylene fabric; a drain (FIG. 10) which may include a housing 20, say, of plastic, beneficially which is clear; top perforated plate 21, say, of plastic, which beneficially is clear; one or more layers of fabric 22, say, of a knitted polyester, which may be by a perforated plate ring 22R; one or more bed layers of the particles 30 and the encapsulated composition 40; and zero or more suitably constructed internal perforated plates 23, direction plates 24 and/or foam filler layers 25. Stand-off material 50, which may be generally inert yet pervious to the target material, as in, for example, a polypropylene mat, may be provided between an outer layer and a portion of the device 100 having the composition 40, which material 50 may provide a barrier, as it were, to non-target induced leakage of the indicator dye from the encapsulating material, were any such leakage to occur, so that a leaked dye as may occur, for instance, from high temperature and/or long term storage, does not color the outer environment and provide a false positive color (FIG. 11). Further forms or shapes in which the invention may be embodied may include pipes, pillows, booms, blankets, pouches, valves, and loose bead-sand mixtures (FIGS. 12A-12F). Numerous other forms or shapes for a device having the encapsulated indicating dye in combination with the sorbent may be employed, among which may be mentioned those of the aforementioned international publication of Hall et al., plus U.S. design Pat. D400973; D400974; D403059; D403060; D403418; D415831; D419652; D428108; and D441067.

An encapsulated indicator dye may be present without sorbent.

As a suitable organic substance comes into contact with the encapsulated indicator dye composition, it releases color. Compare, FIGS. 1-8.

The present invention is thus provided. Various features, parts, steps, subcombinations and combinations can be employed with or without reference to other features, parts, steps, subcombinations or combinations in the practice of the invention, and numerous adaptations and modifications can be effected within its spirit, the literal claim scope of which is particularly pointed out as follows:

What is claimed is:

1. A composition of matter comprising an indicating dye encapsulated by an encapsulating material so as to provide an encapsulated dye composition, wherein:
   the indicating dye is hydrophobic and organo- or oleophilic and is selected from the class of anthracene, azo, anthraquinone, pyrazoline and quinone dyes and a combination whereof;
   the encapsulating material includes an acrylate polymer or copolymer, and is soluble in at least one liquid selected from the group consisting of acetone, gasoline, benzene, toluene, octane, heptane, hexane, pentane, kerosene, diesel fuel, a jet fuel, mineral of heating oil, light machine oil, motor oil, transformer oil, crude oil, distillation bottoms and reactor bottoms; and
   the encapsulated dye composition is in a form of a particle about from fifty to two thousand microns in diameter.

2. The composition of claim 1, wherein the indicating dye and the encapsulating material are present in a plurality of ratios of indicating dye to encapsulating material such that the encapsulated dye composition can be for indication of a plurality of target organic substances that may be expected to be encountered in the field.

3. The composition of claim 1, wherein the indicating dye includes Solvent Red 24, Retinol 50C, and/or Solvent Red 26; the encapsulating material includes the acrylate copolymer; and the indicating dye and the encapsulating material are present in a ratio of indicating dye to encapsulating material of about from 10:1 to 1:10 by weight.

4. A combination, which comprises an indicating dye encapsulated by an encapsulating material so as to provide an encapsulated dye composition; and an organic substance sorbent—wherein:
   the indicating dye is hydrophobic and organo- or oleophilic, and is selected from the class of anthracene, azo, anthraquinone, pyrazoline and quinone dyes and a combination whereof;
   the encapsulating material includes an acrylate polymer or copolymer, and is soluble in least one liquid selected from the group consisting of acetone, gasoline, benzene, toluene, octane, heptane, hexane, pentane, kerosene, diesel fuel a jet fuel, miners oil, heating oil, light machine oil, motor oil, transformer oil, crude oil, distillation bottoms and reactor bottoms; and
   the encapsulated dye composition is in a form of a particle about from fifty to two thousand microns in diameter.

5. The combination of claim 4, wherein the organic substance sorbent eludes an absorbent.

6. The combination of claim 5, wherein the absorbent includes an imbibing polymeric material, which includes a lightly cross-linked polyalkylstyrene copolymer.

7. The combination of claim 6, wherein the indicating dye includes Solvent Red 26.

8. The combination of claim 6, wherein the indicating dye and the encapsulating material are present in a plurality of ratios of indicating dye to encapsulating material such that the encapsulated dye composition can be for indication of a plurality of target organic substances expected to be encountered in the field.

9. The combination of claim 8, wherein the indicating dye and the encapsulating material are present in a ratio of indicating dye to encapsulating material of about from 10:1 to 1:10 by weight.

10. The combination of claim 6, wherein the indicating dye and the encapsulating material are present in a ratio of indicating dye to encapsulating material of about from 10:1 to 1:10 by weight.

11. The combination of claim 6, wherein the indicating dye includes Solvent Red 24, Retinol 50C, and/or Solvent Red 26; the encapsulating material includes the acrylate copolymer; and the indicating dye and the encapsulating material are present in a ratio of indicating dye to encapsulating material of about from 10:1 to 1:10 by weight.

12. The combination of claim 4, which is contained in a suitable device.

13. The combination of claim 12, wherein the device is selected from the group consisting of a packet; a drain; a pipe; a pillow; a boom; a blanket; a pouch; and a valve.

14. The combination of claim 4, wherein the indicating dye and the encapsulating material are present in a plurality of ratios of indicating dye to encapsulating material such that the encapsulated dye composition can be for indication of a plurality of target organic substances expected to be encountered in the field.

15. The combination of claim 14, wherein the indicating dye and the encapsulating material are present in a ratio of indicating dye to encapsulating material of about from 10:1 to 1:10 by weight.

16. The combination of claim 4, wherein the indicating dye and the encapsulating material are present in a ratio of indicating dye to encapsulating material of about from 10:1 to 1:10 by weight.

17. The combination of claim 4, wherein the indicating dye includes Solvent Red 24, Retinol 50C, and/or Solvent Red 26; the encapsulating material includes the acrylate copolymer; and the indicating dye and the encapsulating material are present in a ratio of indicating dye to encapsulating material of about from 10.1 to 1:10 by weight.

18. The combination of claim 17, wherein the indicating dye includes Solvent Red 26.

* * * * *